United States Patent [19]

Diefenbach

[11] Patent Number: 5,600,004

[45] Date of Patent: Feb. 4, 1997

[54] PROCESS FOR PREPARING PENTAFLUOROPHENYL COMPOUNDS

[75] Inventor: Steven P. Diefenbach, Baton Rouge, La.

[73] Assignee: Albemarle Corporation, Richmond, Va.

[21] Appl. No.: 391,806

[22] Filed: Feb. 21, 1995

[51] Int. Cl.$^6$ .................................................. C07F 5/02
[52] U.S. Cl. .................................................. 568/1
[58] Field of Search ...................................... 568/1

[56] References Cited

U.S. PATENT DOCUMENTS

| | | | |
|---|---|---|---|
| 2,853,525 | 9/1958 | Wittig et al. | 260/606.5 |
| 2,880,242 | 3/1959 | Hennion | 260/606.5 |
| 2,880,243 | 3/1959 | Hennion | 260/606.5 |
| 2,939,885 | 6/1960 | Perrine, Jr. | 260/606.5 |
| 3,100,181 | 8/1963 | Ryznar et al. | 204/59 |
| 3,397,241 | 8/1968 | Smai et al. | 260/606.5 |
| 3,405,179 | 10/1968 | Wowk | 260/606.5 |
| 3,475,496 | 10/1969 | Smai et al. | 260/605.6 |
| 5,362,423 | 11/1994 | Ikeda et al. | 260/665 R |
| 5,387,727 | 2/1995 | Ikeda et al. | 570/143 |
| 5,399,780 | 3/1995 | Ikeda et al. | 568/1 |

FOREIGN PATENT DOCUMENTS

| | | |
|---|---|---|
| 0520732 | 12/1992 | European Pat. Off. . |
| 0604959 | 7/1994 | European Pat. Off. . |
| 0604961 | 7/1994 | European Pat. Off. . |
| 0604963 | 7/1994 | European Pat. Off. . |

OTHER PUBLICATIONS

Massey, A. G. et al., J. Organometal. Chem., 2, (1964) 245–250.
Pohlmann, J. L. et al., Z. Naturfurschg. 206, 5–11 (1965).
Harper, R. J., Jr. et al., J. Org. Chem., 29, (1964) 2385–2389.
Respers et al., J. Organometal. Chem., 11 (1968) 619–622.
CA 139179s, vol. 100, No. 17, (1984).

*Primary Examiner*—Paul J. Killos
*Attorney, Agent, or Firm*—Philip M. Pippenger

[57] ABSTRACT

An improved process for recovering pentafluorophenyl metal or metalloid compounds prepared by reacting pentafluoromagnesium halides with a metal or metalloid halide in ether solutions uses a precipitating agent such as an ether to precipitate the by-products from the reaction mixture.

10 Claims, No Drawings

PROCESS FOR PREPARING PENTAFLUOROPHENYL COMPOUNDS

This invention relates generally to the preparation of pentafluorophenyl compounds and more specifically to an improved process for recovering pentafluorophenyl metal and metalloid compounds from ether complexes of such compounds and salt by-products.

Pentafluorophenyl compounds such as tris(pentafluorophenyl)borane and tetrakis(pentafluorophenyl)borates are useful in forming olefin polymerization catalyst complexes with metallocenes. It is known to prepare these compounds by reacting pentafluorophenylmagnesium derivatives with boron halides. The pentafluorophenylmagnesium intermediates can be prepared, for example, by an exchange reaction by reacting ether pentafluorobromobenzene or pentafluorobenzene with an alkylmagnesium halide in an ether solvent. The initial result of the boron halide reaction is an ether solution in which the products and by-product magnesium salts are in the form of an ether complex. The salts can be precipitated by a solvent exchange using a hydrocarbon solvent which boils above the boiling point of the ether solvent. However, these heavy salts have been found to cause serious damage to the agitators in the reaction. It has now been found that the presence of certain organic compounds, and especially ethers, prior to solvent exchange will cause the salts to precipitate without interfering with product recovery.

In accordance with this invention there is provided a process for preparing a pentafluorophenyl compound having the formula $(C_6F_5)_nY$, where Y is a transition or main group element of Groups 4 to 14 of the Periodic Table other than carbon and n equals the valence of Y, said process comprising (a) reacting pentafluorophenylmagnesium halide with a halide of Y in an ether solvent under conditions to form a reaction mixture which contains said pentafluorophenyl compound and a magnesium halide salt, (b) including a precipitating agent in said reaction mixture which is effective to precipitate said salt from said reaction mixture, and (c) separating the precipitated salt from said reaction mixture.

The precipitating agent can be present during the reaction such that the salt precipitates as it is formed or it can be added after the reaction has been completed.

The pentafluorophenylmagnesium halides can be prepared by a Grignard exchange reaction in which, for example, pentafluorobenzene is reacted with an alkylmagnesium bromide in an ether solvent such as is described by Respess et al. in J. Organometal. Chem., 11 1968 619–622, "Synthesis of some pentafluorophenylmagnesium compounds," and Harper et al. in J. Org. Chem., 29, 1964 2385–2389, "Reactions of Organometallics with Fluoroaromatic Compounds." Alternatively, pentafluorobromobenzene can be reacted with an alkylmagnesium bromide.

The pentafluorobenzene or pentafluorohalobenzene is reacted with a hydrocarbylmagnesium halide represented by the general formula RMgX where X is halogen, and preferably bromine or iodine and R is a $C_1$ to $C_{20}$, and preferably a $C_2$ to $C_{10}$, hydrocarbyl group such as, for example ethyl, propyl, propenyl, butyl, pentyl, hexyl, heptyl, octyl, nonyl, decyl, including their branched chain isomers such as, for example, isopropyl, isopropenyl, sec-butyl, tert-butyl, isobutyl, isopentyl, and cyclic alkyls such as for example, cyclohexyl and the like. Most preferred is isopropyl.

The amounts of reactants used can vary from stoichiometric amounts. Preferably, the pentafluorobenzene compound to alkylmagnesium halide mole ratios range from about 1:1 to 10:1 and most preferably from about 1:1 to 2:1 in order to maximize the conversion of the alkylmagnesium halide and minimize side reactions such as the substitution of an alkyl group on the phenyl ring.

The reaction is carried out in an ether solvent. Non-limiting examples of suitable ethers include diethyl ether, dipropyl ether, diisopropyl ether, dibutyl ether, ethylene glycol, dimethyl ether, 2-methoxyethyl ether, tetrahydrofuran and the like. Preferred is diethyl ether which, contrary to the suggestions in the art, provides excellent yields and is more easily separated from the final pentafluorophenylmetal and metalloid products as it does not form as strong complexes as tetrahydrofuran.

The reaction can be carried out in a batch process or by slowly feeding one reagent into the other at a temperature of from about −40° to 100° C. and then the mixture is reacted at temperatures of from about 20° to 250° C. The reaction can be run at atmospheric pressure but, preferably is carried out in a sealed reactor to avoid loss of solvent, in which case the release of solvent vapors and gaseous by-products into the sealed reactor will cause the pressure to increase. Reaction times of from about 0.5 to 50 hours or longer are used to complete the reaction depending upon the temperature used.

The pentafluorophenyl derivatives of transition metal and main group metalloid elements, for example, boron derivatives such as tris(pentafluorophenyl)boron and tetrakis(pentafluorophenyl)borates are formed by reacting the pentafluoromagnesium halide intermediates with metal or metalloid halides such as $BF_3$.

The pentafluorophenyl derivatives can be represented by the general formulas $(C_6F_5)_nY$ (I) and $(C_6F_5)_{n+1}YMgX$ (II) where n is the valence of Y, X is halogen and Y is a transition or main group element of Groups 4 to 14 of the Periodic Table according to the new IUPAC notation. Non-limiting examples of the elements include titanium, zirconium, hafnium, vanadium, chromium, magnesium, iron, ruthenium, zinc, copper, aluminum, boron, silicon and the like. Halides of these elements $(YX_n)$ such as aluminum chloride and boron trifluoride and the like are reacted with the pentafluorophenylmagnesium halides in molar proportions to selectively produce primarily compounds of either formula I, $(C_6F_5)_nY$, or formula II, $(C_6F_5)_{n+1}YMgX$. The non-selected compound $(C_6F_5)_nY$ is usually produced in at least small amounts as a by-product. Compounds of formula (I) are preferentially produced by selecting mole ratios of pentafluorophenylmagnesium halide to $YX_n$ compounds of from about (0.8 to 1.2)n to 1 and compounds of formula II are preferentially produced by selecting mole ratios of at least about 1.25n to 1 and preferably from about (1.25 to 1.5)n to 1.

The reaction is carried out in an ether solvent and the same ethers used in the reaction to form the pentafluorophenylmagnesium bromide are suitable. In fact, the halide reactant can be conveniently added to the pentafluorophenylmagnesium bromide reaction mixture, preferably as its ether complex, at temperatures of from about −40° to 200° C. and then the reaction is completed at temperatures of from about 20° to 250° C. for times ranging from 0.5 to 50 hours or longer, depending upon the temperature.

The products can be recovered by solvent exchange techniques. For example a hydrocarbon solvent which has a higher boiling point is added to the reaction mixture and the ether is removed by azeotropic distillation leaving a hydrocarbon solution of the formula I product and a precipitate of the magnesium halide salt and the formula II co-product. As discussed above, the relative proportion of each product obtained will depend upon the mole ratio of reactants. The solution of the formula I product is then separated from the precipitate and the formula II co-product can be separated from the inorganic magnesium salts by solvent extraction, such as with diethyl ether. The heavy precipitate may damage the agitators during the solvent exchange step. Therefore, according to the invention, a precipitating agent is added to the reaction mixture, which effectively breaks up the ether complex of the product and salts and thereby precipitates the majority of the salts, such that 80 to 90% of the salts can be removed such as by filtration, prior to the solvent exchange step while leaving the formula I product in solution. Preferred precipitating agents are ethers which contain from about 4 to 20 carbon atoms. Non-limiting examples of suitable ethers are alkyl and aryl monoethers such as diisopropyl ether, di-n-butyl ether, methyl tert-butyl ether, diphenyl ether, diethers such as dimethoxyethane, and cyclic ethers such as 1,4-dioxane, 1,3-dioxolane, 2-methyl-1,3-dioxolane, N-methylmorpholine, and triethers such as 1,3,5-trioxane and the like. Tetrahydrofuran is not effective to precipitate the salts. The precipitating agent is added in amounts of from about 0.1 to 1 mole per mole of magnesium such that little or none of the precipitating agent becomes complexed with the formula I product.

The precipitating agent can be present during the reaction such that the salt precipitates as it is formed or it can be added after the reaction has been completed.

Suitable hydrocarbon solvents for the solvent exchange are selected such that a solvent is used that boils above the boiling point of the ether solvent such that the ether is removed as an azeotrope to leave a solution of the formula I product in the hydrocarbon solvent and a precipitate of the remaining magnesium salts and the formula II product. The latter product can be separated from the salts by an ether extraction after separating the precipitate from the product solution such as by filtration of the hot hydrocarbon solvent solution. Non-limiting examples of suitable hydrocarbon solvents having boiling points of from about 65° to 200° C. include hexane, heptane, Isopar E, octane, nonane, decane, hexadecane, benzene, toluene, xylenes, and the like, including mixtures. The hydrocarbon solvent is used in proportions of from about 50 to 99 percent by volume of the total volume of product solution.

The invention is further illustrated by, but is not intended to be limited to, the following examples.

EXAMPLE 1

Step 1
Preparation of $C_6F_5MgBr$ from $C_6F_5H$/isopropylMgBr

A Fisher-Porter glass pressure reactor equipped with magnetic stir bar was charged with 38.77 g (230.69 mmoles) of $C_6F_5H$, 3.00 g (20.53 mmoles) of trifluorotoluene ($CF_3C_6H_5$) internal standard, and 76.8 g (164.8 mmoles) of i-PrMgBr (2.0 molar in diethyl ether). The vessel was capped then placed into a preheated oil bath at 62° C. The mixture was heated at 61°–63° C. for 5–6 hours then cooled to room temperature. The propane by-product was carefully vented from the reaction vessel. An aliquot (1 mL) of the resulting mixture was removed and analyzed by both $^{19}F$ and $^1H$ NMR. The $^{19}F$ NMR showed a 98.8% conversion to $C_6F_5MgBr$ versus the $CF_3C_6H_5$ internal standard. The $^1H$ NMR showed a 99.9% consumption of i-PrMgBr versus the $CF_3C_6H_5$ internal standard.

Step 2
Conversion of $C_6F_5MgBr$ to $(C_6F_5)_3B \cdot Et_2O$

The $C_6F_5MgBr$ (162 mmoles) in ether solution from Step 1 was transferred to a 500-mL Schlenk flask equipped with a magnetic stir bar. To the flask was placed a dropping funnel containing 7.27 g (51.2 mmoles) of $BF_3 \cdot Et_2O$. The flask was removed from the drybox and placed under nitrogen. The solution was cooled at 0° C. with ice/water. The $BF_3 \cdot Et_2O$ was added dropwise very slowly over about 30 minutes. After addition was complete the mixture was allowed to warm to 25° C. and stir overnight. An aliquot (1 mL) of the resulting solution was analyzed by $^{19}F$ NMR. The $^{19}F$ NMR showed about 35–36 mmole of $(C_6F_5)_3B$ etherate complex (~70% yield).

Step 3
MgBrF salt removal with 1,4-dioxane

The $(C_6F_5)_3B$ etherate complex solution (116 g, 100 mL) was diluted with 400 g of ether. As the solution was stirred, 1,4-dioxane (82 mmoles, 7.2 g, 50 mol % relative to iPrMgBr) was added dropwise at 25° C. An immediate precipitate formed during the addition. After addition was complete, the resulting slurry was stirred for 30 minutes. The cream-colored solid precipitate was filtered onto a medium glass filter frit and washed with 50 ml of ether. The filtrates were combined and analyzed by $^{19}F$ NMR. The $^{19}F$ NMR showed 36 mmoles of $(C_6F_5)_3B$ ether complex present versus the $CF_3C_6H_5$ internal standard. None of the complex was lost as a result of the dioxane addition. Thus, there was neither removal of $(C_6F_5)_3B$ etherate complex to the MgBrF salt nor was there formation of a $(C_6H_5)_3B$ dioxane complex. Dioxane was complexed to Mg as a MgBrF dioxane ether complex. Analysis of the isolated salt by $^1H$ NMR in $D_2O$ solvent showed both dioxane (4.0 ppm, singlet) and ether (3.5 ppm quartet and 1.1 ppm triplet) signals. Adding an additional 25 mol % dioxane caused more MgBrF salt to precipitate but no loss of $(C_6F_5)_3B$ etherate was seen by NMR. The resulting $(C_6F_5)_3B$ etherate solution, now containing only minor amounts of soluble MgBrF, can undergo solvent exchange with, for example, heptane, Isopar E, toluene, etc., to free the $(C_6F_5)_3B$ from its ether complex without any complications resulting from the MgBrF salts.

EXAMPLE 2

A $(C_6F_5)_3B$ etherate solution containing the soluble MgBrF salt was prepared as in Example 1. Analysis of this solution by $^{19}F$ NMR ($CF_3C_6H_5$ internal standard) showed 10.4 wt % $(C_6F_5)_3B$ as its etherate (20.3 mmoles $(C_6F_5)_3B$ etherate per 100 grams solution). 100 grams of this solution (20.3 mmoles $(C_6F_5)_3B$ etherate complex) were placed into a 500 mL Schlenk flask equipped with a stir bar. The solution was diluted with 100 g ether. To the stirred solution was added 6.0 g (81.2 mmoles) of 1,3-dioxolane dropwise at 25° C. A cream-colored solid precipitated during the addition. After the addition was complete, the resulting slurry was stirred at 25° C. for 15 minutes then filtered onto a coarse filter frit then washed with 50 ml of ether. The combined filtrates were analyzed by $^{19}F$ NMR. The $^{19}F$ NMR showed 21 mmoles of $(C_6F_5)_3B$ as its etherate complex. No loss of $(C_6F_5)_3B$ etherate was observed. 1,3-Dioxolane was not detected in the $^1H$ NMR. Thus, 1,3-dioxolane complexed to the soluble MgBrF to give an insoluble MgBrF 1,3-dioxolane complex but did not complex to the $(C_6F_5)_3B$ ether complex to give a $(C_6F_5)_3B$ 1,3-dioxolane complex. The resulting $(C_6F_5)_3B$ etherate solution now contained only minor amounts of soluble MgBrF. The solution of $(C_6F_5)_3B$ etherate can undergo solvent exchange with, for example, octane, heptane, Isopar E, etc. to free the $(C_6F_5)_3B$ from its ether complex to give a octane, heptane, Isopar E, etc.

solution of $(C_6F_5)_3B$ without complications of large amounts of MgBrF salts.

What is claimed is:

1. A process for preparing a pentafluorophenyl compound having the formula $(C_6F_5)_nY$, where Y is a transition or main group element of Groups 4 to 14 of the Periodic Table other than carbon and n equals the valence of Y, said process comprising (a) reacting pentafluorophenylmagnesium halide with a halide of Y, in mole ratios of pentafluorophenylmagnesium halide to said halide of Y of from (0.8 to 1.2) n to 1, in an ether solvent under conditions to form a reaction mixture which contains said pentafluorophenyl compound and a magnesium halide salt, (b) including a precipitating agent in said reaction mixture which is effective to precipitate said salt from said reaction mixture, and (c) separating the precipitated salt from said reaction mixture.

2. The process of claim 1 wherein said precipitating agent is present during reaction such that said salt precipitates as it is formed.

3. The process of claim 1 wherein said precipitating agent is added to the reaction mixture.

4. The process according to claim 1 wherein a pentafluorophenylmagnesium halide is reacted with $BF_3$ and said pentafluorophenyl compound is $(C_6F_5)_3B$.

5. The process according to claim 1 wherein said precipitating agent is an ether.

6. The process according to claim 5 wherein said ether is a cyclic ether selected from the group consisting of 1,4-dioxane, 1,2-dioxolane, 1,3-dioxolane, 2-methyl-1,3-dioxolane, trioxane and N-methylmorpholine.

7. The process according to claim 5 wherein said ether is 1,4-dioxane.

8. The process according to claim 5 wherein said ether is 1,3-dioxolane.

9. The process according to claim 1 wherein said precipitating agent is added in amounts of from about 0.1 to 1 mole per mole magnesium.

10. The process according to claim 1 wherein after step (c) a hydrocarbon solvent which has a boiling point higher than said ether is added and the ether solvent is removed by distillation to provide a hydrocarbon solvent solution of said pentafluorophenyl compound.

* * * * *